United States Patent [19]

Fujioka et al.

[11] Patent Number: 5,605,153
[45] Date of Patent: Feb. 25, 1997

[54] MEDICAL IMAGE DIAGNOSTIC SYSTEM

[75] Inventors: Yoshio Fujioka, Tochigi-ken; Masakazu Osada, Ootawara; Chikayoshi Yuzawa, Yaita, all of Japan

[73] Assignee: Kabushiki Kaisha Toshiba, Kawasaki, Japan

[21] Appl. No.: 368,054

[22] Filed: Jan. 3, 1995

Related U.S. Application Data

[63] Continuation of Ser. No. 77,933, Jun. 18, 1993, abandoned.

[30] Foreign Application Priority Data

Jun. 19, 1992 [JP] Japan ..................... 4-160963

[51] Int. Cl.$^6$ ...................... A61B 5/05
[52] U.S. Cl. ............ 128/653.1; 395/924; 382/128
[58] Field of Search .......... 364/413.13, 413.02; 395/200.01, 600, 924; 382/128, 131, 132; 128/653.1

[56] References Cited

U.S. PATENT DOCUMENTS

| | | | |
|---|---|---|---|
| 4,458,267 | 7/1984 | Dolazza | 358/111 |
| 4,603,254 | 7/1986 | Tokano et al. | 250/327.2 |
| 4,672,683 | 6/1987 | Matsueda | 382/57 |
| 4,817,050 | 3/1989 | Komatsu et al. | 395/600 |
| 4,835,690 | 5/1989 | Gangarosa | 364/413.13 |
| 4,855,910 | 8/1989 | Bohning | 364/413.13 |
| 4,876,643 | 8/1989 | McNeill et al. | 395/200 |
| 4,958,283 | 9/1990 | Tawara et al. | 364/413.13 |
| 5,019,975 | 5/1991 | Mukai | 364/413.13 |
| 5,140,518 | 8/1992 | Ema | 364/413.13 |
| 5,272,625 | 12/1993 | Nishihara et al. | 364/413.13 |

*Primary Examiner*—Marvin M. Lateef
*Assistant Examiner*—Brian L. Casler
*Attorney, Agent, or Firm*—Oblon, Spivak, McClelland, Maier & Neustadt, P.C.

[57] ABSTRACT

In a medical image diagnostic system of this invention having at least an image collecting section, an image storing section, a display section, and an image processing section, the system further includes a determining section and an adding section. The determining section determines an image as an important image when an image derived from the image collecting section and an image stored in and read out from the image storing section satisfy a predetermined important image determining condition when the images are supplied via the image collecting section, image storing section, display section and image processing section. The adding section adds preset identification information to the image which is determined as an important image by the determining section.

19 Claims, 5 Drawing Sheets

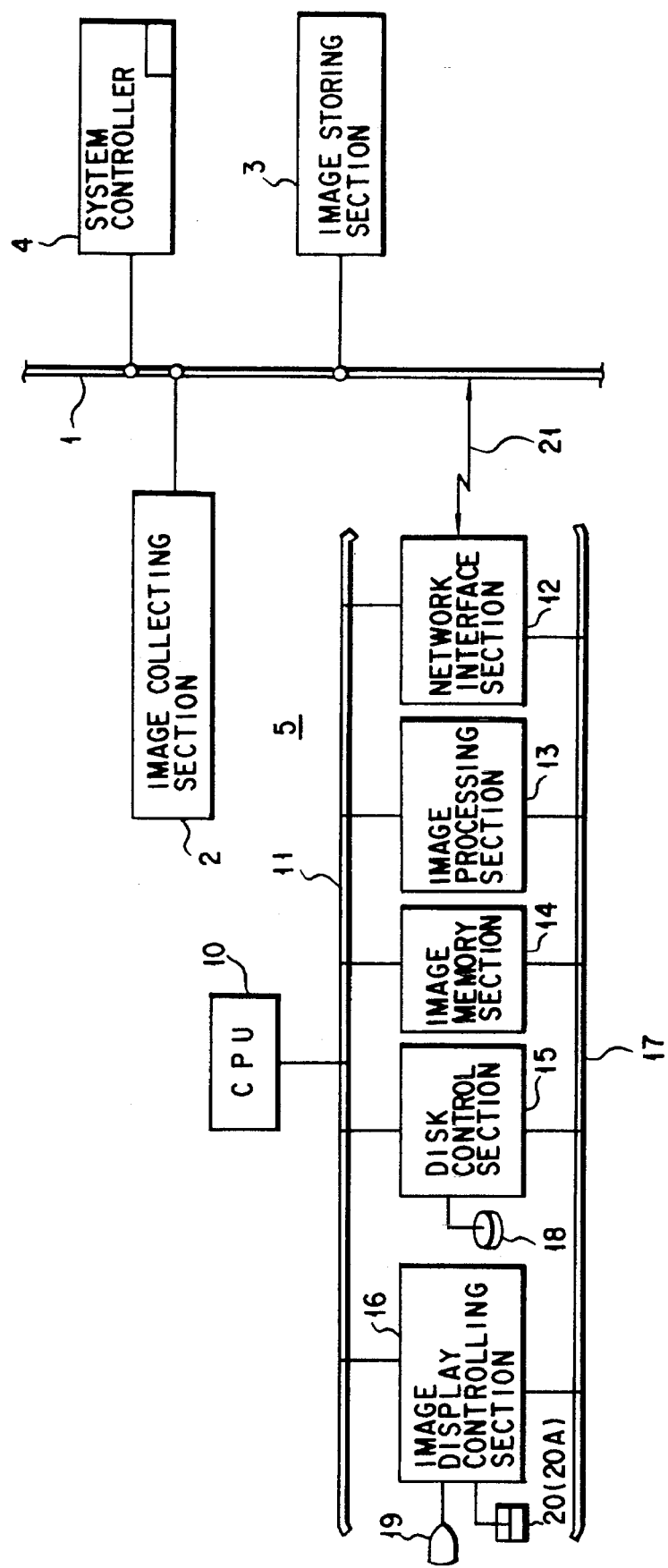
F I G. 1

| PAST EXAMINATION / PRESENT EXAMINATION | | CT | | MRI | XR | CONTRAST ENHANCEMENT | | | | | |
|---|---|---|---|---|---|---|---|---|---|---|---|
| | | ONE TEST BEFORE | TWO TESTS BEFORE | | | ANGIO. | ALIMENTARY | PANCREAT. | URETER | MYELO. | US |
| CT | HEAD | 1 | 5 | 2 | 4 | 3 | * | * | * | * | * |
| | CHEST | 1 | 5 | 3 | 2 | * | 4 | * | * | * | * |
| | ABDOMEN | 1 | * | 7 | 2 | * | 4 | 5 | 6 | * | 3 |
| | PELVIS | 1 | * | 2 | 6 | * | * | 3 | 4 | * | 5 |
| | SPINE | 1 | 5 | 2 | 3 | * | * | * | * | 4 | * |
| | HAND AND FOOT | 1 | * | 3 | 2 | 4 | * | * | * | * | * |
| MRI | HEAD | | | | | | | | | | |
| | CHEST | | | | | | | | | | |

MEDICAL IMAGE DIAGNOSTIC SYSTEM

This application is a continuation of application Ser. No. 08/077,933, filed on Jun. 18, 1993, now abandoned.

BACKGROUND OF THE INVENTION

1. Field of the Invention

This invention relates to a medical image diagnostic system for making a medical diagnosis of a subject based on images obtained by a medical image collecting device.

2. Description of the Related Art

In a medical image collecting device such as an X-ray CT scanner device (CT), magnetic resonance imaging device (MRI) or X-ray imaging device (XR), a plurality of image pictures of various objects (heart, stomach, head and the like) of the same patient are taken. In this case, the object (diseased part) is photographed by use of the various medical image collecting devices according to the diagnostic method. For example, the pictures are taken by CT, MRI or XR, or the pictures are taken by contrast enhancement. Further, the photographing portion may be divided into the chest, head, abdominal portion, anglo, and alimentary canal of a human body according to diseased portions. Therefore, a plurality of image pictures are taken for a single patient for different medical image collecting devices and different diseased portions. Thus, the obtained image data is stored in an image storing device such as a magnetic disk device.

In a case where a diagnosis is made for a patient and if a plurality of image pictures were taken by CT, for example, when the patient was present at the hospital before and the image data was stored, then the doctor compares images of the diseased portion taken at this time with the images of the diseased portion stored and makes a diagnosis based on the result of the comparison.

In this case, the doctor selects image data necessary for the diagnosis from the plurality of stored image data items to display the selected image data on a CRT display.

However, with the above diagnostic method, the doctor must select image data necessary for the diagnosis from the plurality of stored image data items to display the selected image data on a display. It is difficult and troublesome for the doctor to operate the device, and therefore, the doctor cannot concentrate his attention on reading and observing of the images of the diseased portion.

As described above, since the doctor must operate the device to select necessary image data and it is difficult and troublesome for the doctor to operate the device, the doctor cannot concentrate his attention on reading and observation of the images of the diseased portion.

SUMMARY OF THE INVENTION

An object of this invention is to provide a medical image diagnostic system with which only necessary images can be easily selected from a plurality of images and can be displayed in a simple operation.

The above object can be attained by the following medical image diagnostic system. That is, in a medical image diagnostic system having at least an image collecting section, an image storing section, a display section, and an image processing section, the system further comprises determining means for determining an image as an important image when an image derived from the image collecting section and an image stored in and read out from the image storing section satisfy a predetermined important image determining condition; and adding means for adding preset identification information to the image which is determined to be an important image by the determining means.

Further, the above object can be attained by the following medical image diagnostic system. That is, in a medical image diagnostic system having at least an image collecting section, an image storing section, a display section, and an image processing section, the system further comprises important image determining means for determining an image as an important image when an image derived from the image collecting section and an image stored in and read out from the image storing section satisfy a predetermined important image determining condition; priority determining means for determining the priority of an image which is determined to be an important image by the important image determining means according to a preset priority condition; and adding means for adding preset identification information to the image which is determined to be an important image by the important image determining means and whose priority is determined by the priority determining means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram showing one embodiment of a medical image diagnostic system according to this invention;

DETAILED DESCRIPTION OF THE PREFERRED EMBODIMENT

Figures 2, 3:
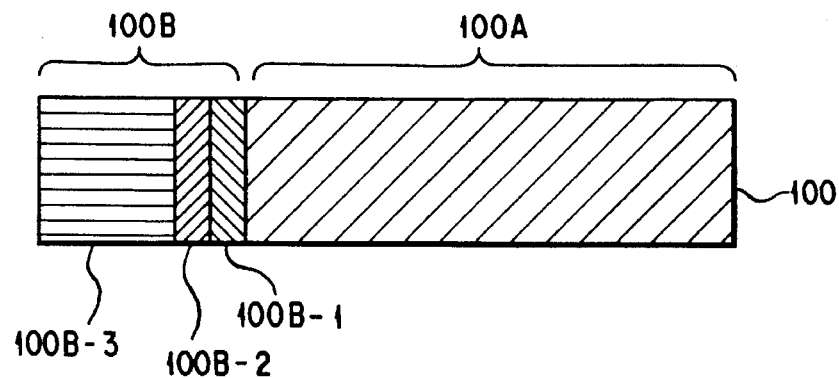
FIG. 2 is a schematic diagram of a priority table in the above system.
FIG. 3 is a diagram showing the data structure of recording data in the above system.

There will now be described an embodiment of this invention with reference to the accompanying drawings.

FIG. 1 is a block diagram showing one embodiment of a medical image diagnostic system according to this invention. A communication line 1 is connected to an image collecting device 2, image storing section 3, system controller 4 and image processing/displaying device 5. Further, the communication line 1 is connected to the image processing/displaying section 5 via a wired or wireless communication line 21.

The image collecting device 2 is connected to the communication line 1. The image collecting device 2 is typically an X-ray CT scanner device (CT), magnetic resonance imaging device (MRI), or X-ray imaging device (XR).

The image storing section 3, such as a magnetic disk memory, stores a large number of images derived from the image collecting device 2. By operating a key input section 20 of the image processing/displaying section 5, a large number of images stored in the image storing section 3 can be selectively read out.

Now, the data structure of data supplied from the image collecting device 2 is explained. An image is transferred from the image collecting device 2 to the image storing section 3 for each recording data. One recording data item is typically shown in FIG. 3. That is, one recording data 100 is constructed by image data 100A and additional data 100B. The additional data 100B includes an important flag portion 100B-1 to be described later, priority data portion 100B-2 to be described later, and auxiliary data 100B-3 such as historical data useful for diagnosis.

Figure 4:
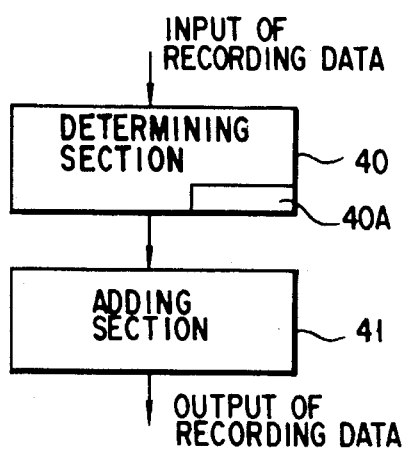
FIG. 4 is a block diagram showing an example of a section having a function of determining an important image in the above system.

In the important flag portion 100B-1, a flag (for example, 1-bit data) is changed from "0" to "1" by means of a determining section 40 and adding section 41 which will be described later and are shown in FIG. 4 when an image (image data 100A) of the recording data satisfies a preset important image determining condition.

Figure 5:
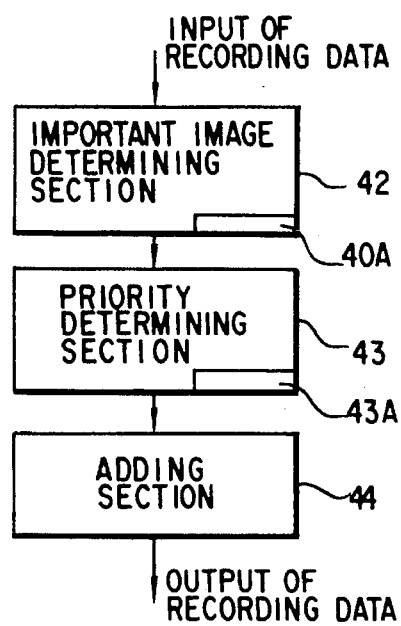
FIG. 5 is a block diagram showing an example of a section having a function of determining an important image and determining the priority in the above system.

In the priority data portion 100B-2, an important flag (for example, 1-bit data) is changed from "0" to "1" by means of an important image determining section 42, priority determining section 43 and adding section 44 which will be described later and are shown in FIG. 5 when an image (image data 100A) of the recording data satisfies a preset important image determining condition and priority data (for example, 2-bit data) is selectively set to "00", "01", "10" or "11" when an image (image data 100A) of the recording data satisfies a preset priority image determining condition. In this case, the priority data of "00" indicates the highest priority and the priority data of "11" indicates the lowest priority. The important flag and priority flag are registered in the image storing section 3 in the table form as shown in FIG. 2.

The image storage format in the image storing section 3 is made as follows. That is, a large number of images are classified according to one of or a combination of the classification for respective patients, classification for the types of the image collecting devices 2, classification for the types of the diagnostic methods, and classification for the types of to-be-diagnosed portions (diseased portions) and stored into the image storing section 3.

Further, additional data to be added to the image data, historical data and the like are stored into the image storing section 3.

The system controller 4 controls the image collecting device 2, image storing section 3 and image processing/displaying section 5. Further, the system controller 4 transfers diagnostic data (images and other diagnostic data) from the image collecting device 2 or image storing section 3 to the image processing/displaying section 5. The system controller 4 further includes a priority table for display of image data items stored in the image storing section 3. FIG. 2 is a schematic diagram showing the priority table. The types of image collecting devices used in the present photographing operation and photographing portions are indicated in the column direction of the priority table of FIG. 2. Further, the types of image collecting devices used in the past photographing operations are indicated in an order of the photographing times in the column direction of the priority table of FIG. 2. The types of the image collecting devices 2 are CT, MRI, XR, and the photographing portions are, for example, a head, chest, and abdomen for each of the image collecting devices 2. Numerals registered in the priority table indicate the priorities and the priority of a smaller numeral has a higher priority.

Next, the image processing/displaying section 5 is explained. When an edition program stored in a CPU 10 is executed, data is input from the system controller 4 to the image processing/displaying section 5. The data is identified by the CPU 10 and then recording data is read out from the image storing section 3 based on the priority according to the table shown in FIG. 2.

Next, the image processing/displaying section 5 is concretely explained. The CPU 10 is connected to a network interface section 12, image processing section 13, image memory section 14, disk control section 15 and image display control section 16 via a CPU bus 11. The network interface section 12, image processing section 13 and image memory section 14 are connected to each other via a high-speed bus 17. Therefore, a command generated from the CPU 10 is transmitted to the network interface section 12 via the CPU bus 11 and data is transferred between the network interface section 12, image processing section 13, image memory section 14 at a high speed.

The network interface section 12 is connected to the communication line 1 via the communication line 21 and acts as an interface for data transfer with respect to the image collecting device 2, image storing section 3 and system controller 4. The image processing section 13 has a function of processing images, for example, reducing and enlarging image data. The disk control section 15 has a function of storing recording data containing image data supplied from the image storing section 3 into the magnetic disk storage device 18 and reading out the recording data from the magnetic disk storage device 18.

Further, the image display controlling section 16 is connected to a CRT display 19 and a key input section 20 having a mouse 20A. The image display controlling section 16 has a function of displaying image data stored in the image memory section 14 on the CRT display 19 and a function of specifying the input of image switching via the key input section 20 containing the mouse 20A.

The CPU 10 controls the operation of the network interface section 12, image processing section 13, image memory section 14, disk control section 15 and image display control section 16. Further, the CPU 10 has a function of determining the important image determining condition. The function is attained by use of the determining section 40 and adding section 41 shown in FIG. 4. The determining section 40 determines an image as an important image when the image derived from the image collecting section 1 and the image stored in and read out from the image storing section 3 satisfy the following important image determining condition. The determining section 40 has important image determining condition data 40A. The adding section 41 sets an important flag of recording data for an image which is determined to be an important image by the determining section 40. The function of determining the important image determining condition is as follows.

(a) The CPU 10 has a function of specifying an important image for image data when the image processing section 13 effects the image processing for the image data stored in the image memory section 14 or magnetic disk storage device 18.

(b) The CPU 10 has a function of specifying an important image for image data when the display position of the image data is changed.

(c) The CPU 10 has a function of specifying an important image for image data which is displayed on the CRT display 19 for more than a previously determined period of time.

(d) The CPU 10 has a function of specifying an important image for image data by manual operation.

Further, the CPU 10 may have a function of determining a priority determining condition in addition to the function of determining the important image determining condition. The function is achieved by use of the important image determining section 42, priority determining section 43 and adding section 44 shown in FIG. 5. The important image determining section 42 is the same as the determining section 40. The priority determining section 43 has priority determining condition data 43A such as the table shown in FIG. 2. Like the adding section 41 described before, the adding section 44 sets the priority and important flag of recording data for an image which is determined to be an important image by the determining section 42 and whose priority is determined by the determining section 43.

Figure 6:
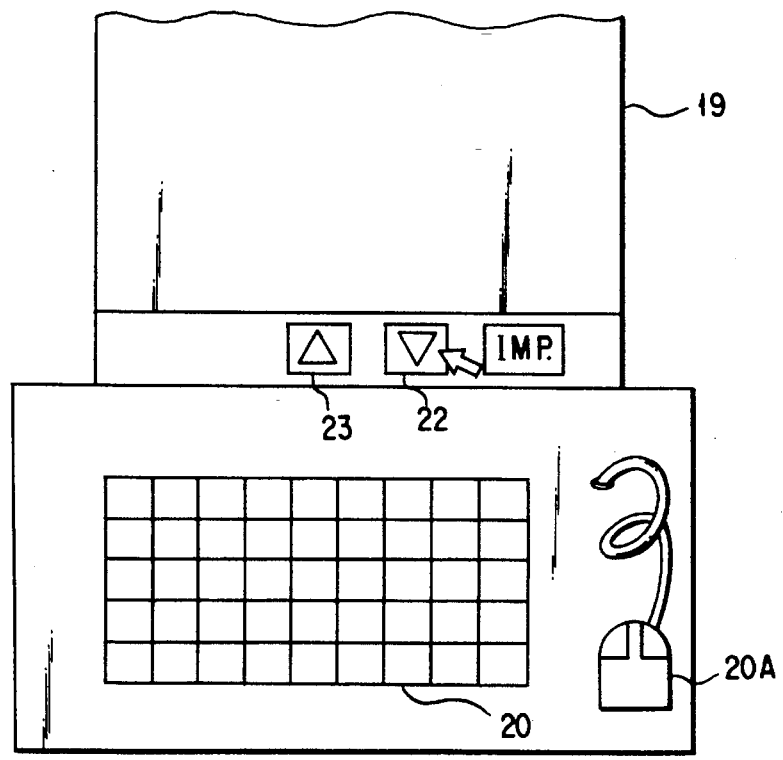
FIG. 6 is a view showing a key input section including a CRT display and a mouse.

As shown in FIG. 6, important image specifying keys 22, 23 are displayed on a control area lying in the lower portion of the display plane of the CRT display 19. The important image specifying keys 22, 23 are operated to select an important image. Image data is selected by operating the important image specifying keys 22, 23, and the contents of this operation are specified by use of the key input section 20 containing the mouse 20A. Then, the image display controlling section 16 sets an important image flag among the image additional data of the image data.

Next, the operation of the device with the above construction is explained. When a diseased portion of a patient is photographed by the image collecting device 2, image data obtained by the photographing operation is stored in the image storing section 3 via the communication line 1. The image storing section 3 stores image data obtained in the preceding photographing operation.

When data is transferred to the image processing/displaying section 5 by means of the system controller 4, the CPU 10 checks the received data, reads out image data obtained in the present photographing operation, adds image additional data to the image data and past report data from the image storing section 3, reads out image data obtained in the preceding photographing operation, reads image additional data and past report data from the image storing section 3, and transfers the above data to the disk control section 15. The disk control section 15 stores recording data constructed by the above image data and additional data into the magnetic disk storage device 18.

Next, the CPU 10 supplies an image display command to the disk control section 15. Then, the disk control section 15 reads out image additional data items for the respective image data items obtained in the preceding photographing operation and stored in the magnetic disk storage device 18 and checks whether the important image flag is set or not. If it is detected that the important image flag is set as the result of the above checking process, the CPU 10 reads out the image data which is obtained in the preceding photographing operation and in which the important image flag is set, image additional data and past report data from the magnetic disk storage device 18 and transfers the above data items to the image memory section 14, and reads out image data which is obtained in the present photographing operation, additional data and past report data from the magnetic disk storage device 18 and transfers the above data items to the image memory section 14. As a result, the image memory section 14 stores the image data items obtained in the present and preceding photographing operations.

Figure 7:
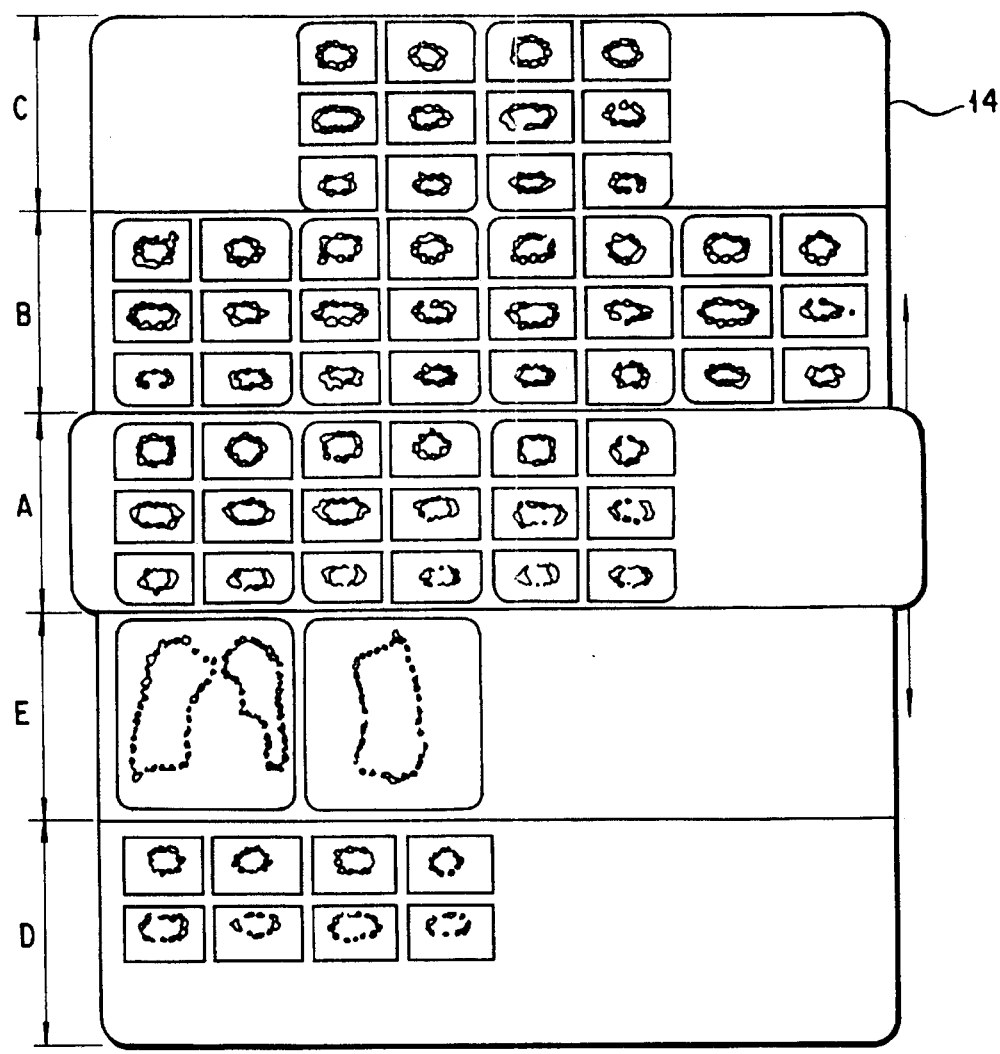
FIG. 7 is a schematic diagram showing an example of the internal structure of an image memory in the above system.

FIG. 7 is a schematic diagram showing the internal area of the image memory section 14. In areas A and B, image data items obtained in the present photographing operation are stored. In an area C, image data items in which the important image flag is set and which are obtained in the preceding photographing operation by use of the CT scanner are stored. In an area D, the newest image data items in which the important image flag is set and which are obtained by use of the X-ray device are stored. Further, in an area E, the newest image data items in which the important image flag is set and which are obtained by use of the MRI are stored. The above image data items are indicated with the inverted black-and-white relation for convenience for the drawing. In a case where four CRT displays 19 are connected, four image data items are stored in each of the areas of the image memory section 14. In this case, three image data items stored in the area A are supplied to the respective CRT displays 19.

In a case where the image data is subjected to the image processing operation such as the enlarging process or reducing process, the CPU 10 supplies an image processing command to the image processing section 13. The image processing section 13 reads out corresponding image data from the image memory section 14 in response to the image processing command, subjects the image data to the image processing operation such as the enlarging process or reducing process, and stores the image data subjected to the image processing operation into the image memory section 14 again.

Figure 8:
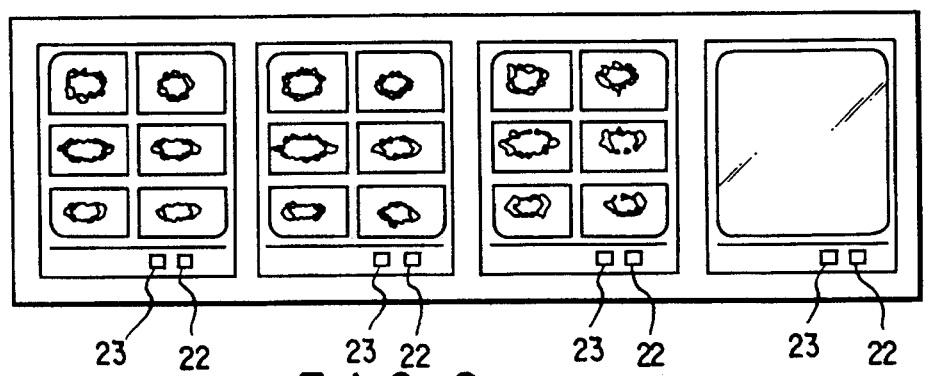
FIG. 8 is a schematic view showing an example of a display image in the above system.

The operation of image display is effected as follows. The CPU 10 supplies a display command to the image display controlling section 16. The image display controlling section 16 reads out three image data items which are stored in the area A and obtained in the present photographing operation, for example, from the image memory section 14 as shown in FIG. 8. Then, the readout image data items are displayed on the four CRT displays 19. In this case, no image data is stored in one of the CRT displays and no display is effected. If, in this condition, the operation of selecting image data to be displayed is effected by use of the mouse 20A, the image display controlling section 16 changes the readout area from A to B, C,—on the image memory section 14 according to the above operation. By the above selecting operation, image data obtained in the preceding photographing operation by use of the CT scanner, newest image data obtained by use of the X-ray device and newest image data obtained by use of MRI are selectively displayed on the four CRT displays 19.

Next, determination of the important image and addition of a flag are explained. The determination of the important image and the addition of a flag are effected by use of the determining section 40 and adding section 41 shown in FIG. 4. First, the image processing section 3 effects the image processing operation according to an image processing command from the CPU 10 as described above to set up a state in which no important image is displayed on the CRT display 19. At this time, the CPU 10 sets the important flag of image data which is subjected to the image processing operation such as the enlarging process or reducing process.

Second, if the operation of changing the order of image data items to be displayed is effected by use of the key input section 20 containing the mouse 20A, the content of the order changing operation is transmitted to the CPU 10 via the display controlling section 16. The CPU 10 receives the content of the order changing operation and supplies a command for setting an important image flag in the image additional data of image data which is subjected to the order changing process to the disk control section 15. As a result, the disk control section 15 sets the important flag of corresponding image data stored in the magnetic disk storage device 18.

Third, when image data is displayed on the CRT display 19 by the image display controlling section 16 for more than a preset period of time, the content of the display is transmitted from the image display controlling section 16 to the CPU 10. The CPU 10 sets the flag of the image which has been displayed for a long period of time as described above.

Fourth, when image data is selected by operating the important image specifying keys 22, 23 and the content of the operation is specified by the key input section 20 containing the mouse 20A, the image display controlling section 16 sets the important flag of the image data.

Next, when the entire operation of reading the image displayed on the CRT display 19 is completed, the disk control section 15 reads out various image data items stored in the image memory section 14, transfers the same image data items to the magnetic disk storage device 18 and then supplies the same image data items back to the image storing section 3.

Therefore, when the above image data is next read out from the image storing section 3, image data selected as the important image is preferentially selected and displayed on the CRT display 19.

In the embodiment described above, when image data is subjected to the image processing operation, when the display position or the display order of respective image data items is changed, or when image data is displayed for more than a preset period of time, the image data is specified as an important image and the important image flag for corresponding image data is set. Therefore, only image data items that are necessary for diagnosis are selected from a plurality of image data items and displayed on the CRT display 19.

Further, when image data is registered as an important image, the image data to be subjected to the image processing operation is processed to derive detail information on the diseased portion and it is therefore an important image. Further, image data whose display position is intentionally changed and image data which is displayed for more than a preset period of time are registered as important image data. Therefore, image data determined as an important image can be automatically selected, necessary image data of the diseased portion can be easily displayed by a simple operation for the next diagnostic process, and the doctor can concentrate his attention on the diagnosis of the diseased portion. Of course, determination of the important image can be manually effected.

This invention is not limited to the above embodiment and can be variously modified without departing from the technical scope thereof. For example, it is not necessary to determine the arrangement order of the storage areas when various image data items are stored in the image memory section and it is possible to directly transfer image data from the magnetic disk storage device 18 to the image display controlling section 16 without storing the same in the image memory section 14.

Figure 9:
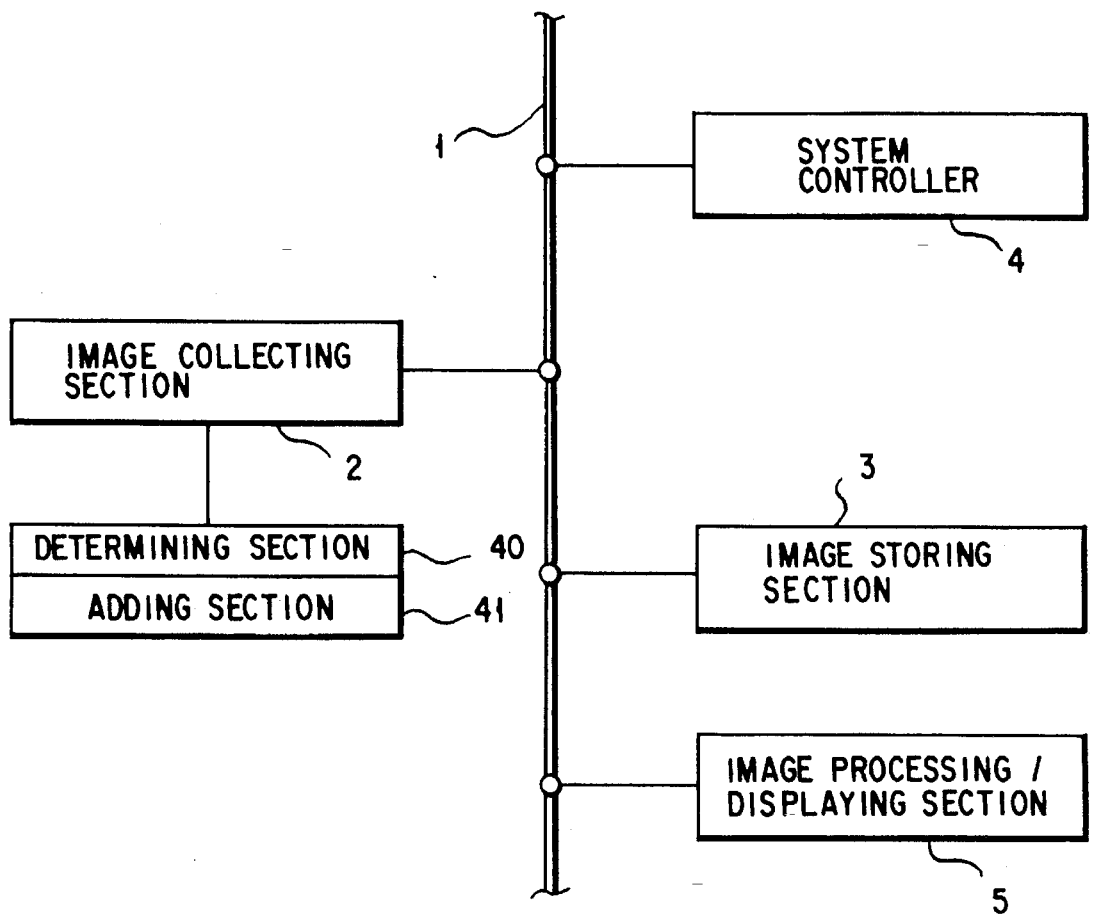
FIG. 9 is a diagram showing a modification of the above system.

Further, as shown in FIG. 9, the determining section 40 and adding section 41 may be connected to the image collecting device 2. With this connection, selection of the important image data may be effected by use of the determining section 40 and adding section 41 and an important flag of the corresponding image data may be set.

As described above, according to this invention, a medical image diagnostic system can be provided in which necessary image data can be easily selected from a plurality of image data items by a simple operation and displayed.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A medical image diagnostic system comprising:
   image collection means for collecting a plurality of images of various objects of the same subject to be examined;
   image storing means for storing said plurality of images by said image collecting means;
   image processing means for processing at least one of said plurality of images in accordance with predetermined conditions;
   display means for displaying at least one of said plurality of images; and
   determining means for determining an image as an important image in accordance with an important image determining condition, said important image determining condition is defined by subjecting an image derived from said image collecting means, stored in said image storing means and read out from said image storing means to a predetermined image processing operation; and
   adding means for adding preset identification information to the image which is determined to be an important image by said determining means.

2. A medical image diagnostic system according to claim 1, further comprising control means for controlling storage and readout of image data stored in said image storing means to preferentially transfer an image having the identification information added thereto among the images stored in said image storing section according to an image selection parameter being defined by use of at least one of patient identifying information, diagnostic item information and to-be-diagnosed object information, when the image selection parameter is specified.

3. A medical image diagnostic system according to claim 1, wherein said adding means includes means for automatically adding preset identification information to an image which is determined as an important image by said determining means.

4. A medical image diagnostic system according to claim 1, wherein said adding means includes means manually operated to add preset identification information to an image which is determined as an important image by said determining means.

5. A medical image diagnostic system according to claim 1, further comprising:

priority determining means for determining a priority of an image which is determined to be an important image by said important image determining means according to a priority condition being defined by use of at least one of patient identifying information, diagnostic item information and to-be-diagnosed object information.

6. A medical image diagnostic system comprising:

image collecting means for collecting a plurality of images of various objects of the same subject to be examined;

image storing means for storing said plurality of images by said image collecting means;

image processing means for processing at least one of said plurality of images in accordance with predetermined conditions;

display means for displaying at least one of said plurality of images; and determining means for determining an image as an important image in accordance with an important image determining condition, said important image determining condition is defined by changing a display position of the image derived from an image collecting means, stored in said image storing means and read out from said image storing means in said image displaying means; and adding means for adding preset identification information to the image which is determined to be an important image by said determining means.

7. A medical image diagnostic system according to claim 6, further comprising control means for controlling storage and readout of image data stored in said image storing means to preferentially transfer an image having the identification information added thereto among the images stored in said image storing section according to a preset image selection parameter when the image selection parameter is specified.

8. A medical image diagnostic system according to claim 7, wherein said image selection parameter is defined by at least one of patient identifying information, diagnostic item information and to-be-diagnosed object information.

9. A medical image diagnostic system according to claim 6, wherein said adding means includes means for automatically adding preset identification information to an image which is determined as an important image by said determining means.

10. A medical image diagnostic system according to claim 6, wherein said adding means includes means manually operated to add preset identification information to an image which is determined as an important image by said determining means.

11. A medical image diagnostic system according to claim 6, further comprising:

priority determining means for determining a priority of an image which is determined to be an important image by said important image determining means according to a preset priority condition.

12. A medical image diagnostic system according to claim 11, wherein said priority condition is defined by at least one of patient identifying information, diagnostic item information and to-be-diagnosed object information.

13. A medical image diagnostic system according to claim 12, further comprising:

priority determining means for determining a priority of an image which is determined to be an important image by said important image determining means according to a preset priority condition.

14. A medical image diagnostic system according to claim 13, wherein said priority condition is defined by at least one of patient identifying information, diagnostic item information and to-be-diagnosed object information.

15. A medical image diagnostic system comprising:

an image collecting means for collecting a plurality of images of various objects of the same subject to be examined;

an image storing means for storing said plurality of images by said image collecting means;

image processing means for processing at least one of said plurality of images in accordance with predetermined conditions;

a display means for displaying at least one of said plurality of images; and determining means for determining an image as an important image in accordance with an important image determining condition, said important image determining condition is defined by displaying an image derived from said image collecting means, stored in said image storing section and read out from said image storing means on said image displaying means for more than a preset period of time; and adding means for adding preset identification information to the image which is determined to be an important image by said determining means.

16. A medical image diagnostic system according to claim 15, further comprising control means for controlling storage and readout of image data stored in said image storing means to preferentially transfer an image having the identification information added thereto among the images stored in said image storing section according to a preset image selection parameter when the image selection parameter is specified.

17. A medical image diagnostic system according to claim 16, wherein said image selecting parameter is defined by at least one of patient identifying information, diagnostic item information and to-be-diagnosed object information.

18. A medical image diagnostic system according to claim 15, wherein said adding means includes means for automatically adding preset identification information to an image which is determined as an important image by said determining means.

19. A medical image diagnostic system according to claim 15, wherein said adding means includes means manually operated to add preset identification information to an image which is determined as an important image by said determining means.

* * * * *